United States Patent
Hapola et al.

(10) Patent No.: US 11,857,842 B2
(45) Date of Patent: *Jan. 2, 2024

(54) APPARATUS AND EXERCISING DEVICE

(71) Applicant: Suunto Oy, Vantaa (FI)

(72) Inventors: Tuomas Hapola, Vantaa (FI); Heikki Nieminen, Vantaa (FI); Mikko Martikka, Vantaa (FI); Erik Lindman, Vantaa (FI); Timo Eriksson, Vantaa (FI)

(73) Assignee: Suunto Oy, Vantaa (FI)

( * ) Notice: Subject to any disclaimer, the term of this patent is extended or adjusted under 35 U.S.C. 154(b) by 0 days.

This patent is subject to a terminal disclaimer.

(21) Appl. No.: 18/072,734

(22) Filed: Dec. 1, 2022

(65) Prior Publication Data

US 2023/0087693 A1 Mar. 23, 2023

Related U.S. Application Data

(63) Continuation of application No. 16/427,394, filed on May 31, 2019, now Pat. No. 11,541,280, which is a
(Continued)

(30) Foreign Application Priority Data

Dec. 21, 2015 (FI) ..................................... 20155989
Dec. 21, 2015 (GB) ..................................... 1522525
(Continued)

(51) Int. Cl.
*A63B 24/00* (2006.01)
*H04W 4/80* (2018.01)
(Continued)

(52) U.S. Cl.
CPC .......... *A63B 24/0087* (2013.01); *A63B 22/02* (2013.01); *A63B 22/0605* (2013.01);
(Continued)

(58) Field of Classification Search
CPC ............ A63B 24/0087; A63B 71/0622; A63B 24/0062; A63B 22/02; A63B 22/0605;
(Continued)

(56) References Cited

U.S. PATENT DOCUMENTS 7,938,752 B1 5/2011 Wang
9,032,321 B1 5/2015 Cohen et al.
(Continued)

FOREIGN PATENT DOCUMENTS

CN 105051494 A 11/2015
CN 106170247 A 11/2016
(Continued)

OTHER PUBLICATIONS

CNET: Dec. 11, 2017, "Apple watch can now sync with a treadmill", youtube.com, [online], Available from: https://www.youtube.com/watch?v=7RvMC3wFDME [ Accessed Nov. 19, 2020].

*Primary Examiner* — Eyob Hagos
(74) *Attorney, Agent, or Firm* — Laine IP Oy

(57) ABSTRACT

According to an example aspect of the present invention, there is provided an apparatus comprising at least one processing core, at least one memory including computer program code, the at least one memory and the computer program code being configured to, with the at least one processing core, cause the apparatus at least to receive a first signal from an exercising device, process the received signal, respond to the received signal by transmitting a second signal to the exercising device, and participate in a pairing process with the exercising device.

20 Claims, 5 Drawing Sheets

Related U.S. Application Data continuation-in-part of application No. 15/386,062, filed on Dec. 21, 2016, now Pat. No. 10,433,768, and a continuation-in-part of application No. 15/386,050, filed on Dec. 21, 2016, now Pat. No. 10,856,776, and a continuation-in-part of application No. 15/386,074, filed on Dec. 21, 2016, now Pat. No. 10,327,673, and a continuation-in-part of application No. 15/382,763, filed on Dec. 19, 2016, now Pat. No. 11,607,144.

(30) Foreign Application Priority Data

| Sep. 20, 2016 | (FI) | .................. | 20165707 |
| Sep. 20, 2016 | (FI) | .................. | 20165709 |
| Sep. 20, 2016 | (FI) | .................. | 20165710 |

(51) Int. Cl.
| *A63B 71/06* | (2006.01) |
| *A63B 22/02* | (2006.01) |
| *G16H 20/30* | (2018.01) |
| *G01P 13/00* | (2006.01) |
| *A63B 22/06* | (2006.01) |

(52) U.S. Cl.
CPC ...... *A63B 24/0062* (2013.01); *A63B 71/0622* (2013.01); *G01P 13/00* (2013.01); *G16H 20/30* (2018.01); *H04W 4/80* (2018.02); *A63B 2071/0625* (2013.01); *A63B 2071/0663* (2013.01); *A63B 2220/803* (2013.01); *A63B 2225/50* (2013.01)

(58) Field of Classification Search
CPC ........ A63B 2225/50; A63B 2071/0625; A63B 2071/0663; A63B 2220/803; A63B 2071/0675; H04W 4/80; G16H 20/30; G01P 13/00

See application file for complete search history.

(56) References Cited

U.S. PATENT DOCUMENTS

| 9,317,660 | B2 | 4/2016 | Burich et al. |
| 9,648,108 | B2* | 5/2017 | Granqvist ............ H04W 48/10 |
| 9,665,873 | B2 | 5/2017 | Ackland et al. |
| 9,923,973 | B2 | 3/2018 | Granqvist et al. |
| 10,065,074 | B1* | 9/2018 | Hoang ................ G09B 19/003 |
| 10,135,905 | B2 | 11/2018 | Chaudhri et al. |
| 10,327,673 | B2 | 6/2019 | Eriksson et al. |
| 10,433,768 | B2 | 10/2019 | Eriksson et al. |
| 2005/0070809 | A1* | 3/2005 | Acres ................ A61B 5/02438 600/508 |
| 2006/0255963 | A1* | 11/2006 | Thompson ............ H04B 1/385 340/12.23 |
| 2008/0136620 | A1 | 6/2008 | Lee et al. |
| 2009/0047645 | A1 | 2/2009 | Dibenedetto et al. |
| 2009/0048070 | A1 | 2/2009 | Vincent et al. |
| 2010/0099539 | A1 | 4/2010 | Haataja |
| 2011/0152695 | A1 | 6/2011 | Granqvist et al. |
| 2011/0218385 | A1 | 9/2011 | Bolyard et al. |
| 2011/0281687 | A1 | 11/2011 | Gilley et al. |
| 2012/0123806 | A1 | 5/2012 | Schumann et al. |
| 2012/0158289 | A1 | 6/2012 | Bernheim Brush et al. |
| 2012/0239173 | A1 | 9/2012 | Laikari et al. |
| 2012/0283855 | A1 | 11/2012 | Hoffman et al. |
| 2013/0127636 | A1 | 5/2013 | Aryanpur et al. |
| 2013/0178334 | A1 | 7/2013 | Brammer |
| 2013/0190903 | A1 | 7/2013 | Balakrishnan et al. |
| 2013/0217979 | A1 | 8/2013 | Blackadar et al. |
| 2013/0218543 | A1 | 8/2013 | Bourgeois et al. |
| 2013/0225370 | A1 | 8/2013 | Flynt et al. |
| 2014/0135593 | A1* | 5/2014 | Jayalth .................. A61B 5/318 600/301 |
| 2014/0142732 | A1 | 5/2014 | Karvonen |
| 2014/0163927 | A1 | 6/2014 | Molettiere et al. |
| 2014/0164611 | A1 | 6/2014 | Molettiere et al. |
| 2014/0228649 | A1 | 8/2014 | Rayner et al. |
| 2014/0235166 | A1 | 8/2014 | Molettiere et al. |
| 2014/0237028 | A1 | 8/2014 | Messenger et al. |
| 2014/0275821 | A1 | 9/2014 | Beckman |
| 2014/0288680 | A1 | 9/2014 | Hoffman et al. |
| 2014/0350883 | A1 | 11/2014 | Carter et al. |
| 2015/0042468 | A1 | 2/2015 | White et al. |
| 2015/0057945 | A1 | 2/2015 | White et al. |
| 2015/0094904 | A1 | 4/2015 | Bourgeois et al. |
| 2015/0180842 | A1* | 6/2015 | Panther .................. A61B 5/681 713/153 |
| 2015/0286285 | A1 | 10/2015 | Pantelopoulos et al. |
| 2015/0317801 | A1 | 11/2015 | Bentley et al. |
| 2015/0334772 | A1* | 11/2015 | Wong .................... H04W 4/025 455/557 |
| 2015/0347983 | A1 | 12/2015 | Jon et al. |
| 2015/0350822 | A1 | 12/2015 | Xiao et al. |
| 2015/0362519 | A1 | 12/2015 | Balakrishnan et al. |
| 2015/0374279 | A1 | 12/2015 | Takakura et al. |
| 2015/0382150 | A1* | 12/2015 | Ansermet ......... H04M 1/72412 455/41.1 |
| 2016/0012294 | A1 | 1/2016 | Bouck |
| 2016/0023043 | A1 | 1/2016 | Grundy |
| 2016/0059079 | A1 | 3/2016 | Watterson |
| 2016/0072557 | A1* | 3/2016 | Ahola ..................... H04W 4/80 455/41.1 |
| 2016/0081625 | A1 | 3/2016 | Kim et al. |
| 2016/0084869 | A1 | 3/2016 | Yuen et al. |
| 2016/0143579 | A1 | 5/2016 | Martikka et al. |
| 2016/0144236 | A1 | 5/2016 | Ko et al. |
| 2016/0184686 | A1 | 6/2016 | Sampathkumaran |
| 2016/0226945 | A1 | 8/2016 | Granqvist et al. |
| 2016/0309409 | A1 | 10/2016 | Lindman et al. |
| 2016/0322078 | A1* | 11/2016 | Bose ...................... G01P 13/00 |
| 2016/0327915 | A1 | 11/2016 | Katzer et al. |
| 2016/0367202 | A1 | 12/2016 | Carter et al. |
| 2017/0010677 | A1 | 1/2017 | Roh et al. |
| 2017/0011210 | A1 | 1/2017 | Cheong et al. |
| 2017/0087431 | A1 | 3/2017 | Syed et al. |
| 2017/0168555 | A1 | 6/2017 | Munoz et al. |
| 2017/0209743 | A1 | 7/2017 | Bengtsson et al. |
| 2017/0266494 | A1 | 9/2017 | Crankson et al. |
| 2018/0015329 | A1 | 1/2018 | Burich et al. |
| 2018/0193695 | A1 | 7/2018 | Lee |
| 2018/0345077 | A1 | 12/2018 | Blahnik et al. |
| 2019/0056777 | A1 | 2/2019 | Munoz et al. |

FOREIGN PATENT DOCUMENTS

| EP | 1755098 | A2 | 2/2007 |
| EP | 2849473 | A1 | 3/2015 |
| TW | M511837 | U | 11/2015 |
| TW | I554266 | B | 10/2016 |
| TW | I598076 | A | 9/2018 |
| WO | WO2014144258 | A2 | 9/2014 |
| WO | WO2016037012 | A1 | 3/2016 |
| WO | WO2018222936 | A1 | 12/2018 |

* cited by examiner

APPARATUS AND EXERCISING DEVICE

RELATED APPLICATIONS

This application is a Continuation of U.S. patent application Ser. No. 16/427,394, filed on May 31, 2019, which is a Continuation-in-Part of U.S. patent application Ser. No. 15/382,763, filed on Dec. 19, 2016, which claims priority to Finnish Patent Application No. 20155989, filed on Dec. 21, 2015. The subject matter of which are incorporated by reference in their entirety.

FIELD

The present invention relates to an apparatus comprising at least one processing core and at least one memory including computer program code. Certain embodiments of the present invention relate to mobile devices such as a wrist-watch, a tablet or a smartphone.

Further, the present invention relates to an exercising device comprising at least one processing core and at least one memory including computer program code. Certain embodiments of the present invention relate to an exercising device such as an ergometer, a gym exercising device, a fitness device, a sports device, a weight lifting device, an exercise bike, a treadmill, a rowing machine, or a cross trainer.

BACKGROUND

Different exercising devices such as ergometers, gym exercising devices, fitness devices, sports devices, weight lifting devices, exercise bikes, treadmills, rowing machines, cross trainers, etc. are known. Some of the known exercising devices are often equipped with an internal display, a user interface and/or a memory, for example exercise bikes or treadmills. Further, various mobile devices are known by means of which information can be stored, processed and/or displayed. The mobile devices typically comprise a user interface such as a touchscreen, a keyboard or at least one button. Examples of such devices are smartphones, tablets, smartwatches and wrist-watches.

User sessions, such as training sessions, may be recorded, for example in notebooks, spreadsheets or other suitable media. Recorded training sessions enable more systematic training, and progress toward set goals can be assessed and tracked from the records so produced. Such records may be stored for future reference, for example to assess progress an individual is making as a result of the training. An activity session may comprise a training session or another kind of session.

Personal devices, such as, for example, smart watches, smartphones or smart jewellery, may be configured to produce recorded sessions of user activity. Such recorded sessions may be useful in managing physical training, child safety or in professional uses. Recorded sessions, or more generally sensor-based activity management, may be of varying type, such as, for example, running, walking, skiing, canoeing, wandering, or assisting the elderly.

Recorded sessions may be viewed using a personal computer, for example, wherein recordings may be copied from a personal device to the personal computer. Files on a personal computer may be protected using passwords and/or encryption, for example.

Personal devices may be furnished with sensors, which may be used, for example, in determining a heart-beat rate of a user during a user session. A recorded heart-beat rate of a user may be later observed using a personal computer, for example.

Document FI 20155989 discloses an apparatus comprising a memory configured to store first-type sensor data, at least one processing core configured to compile a message based at least partly on the first-type sensor data, to cause the message to be transmitted from the apparatus, to cause receiving in the apparatus of a machine readable instruction, and to derive an estimated activity type, using the machine readable instruction, based at least partly on sensor data.

SUMMARY OF THE INVENTION

The invention is defined by the features of the independent claims. Some specific embodiments are defined in the dependent claims.

According to a first aspect of the present invention, there is provided an apparatus comprising at least one processing core, at least one memory including computer program code, the at least one memory and the computer program code being configured to, with the at least one processing core, cause the apparatus at least to receive a first signal from an exercising device, process the received signal, respond to the received signal by transmitting a second signal to the exercising device, and participate in a pairing process with the exercising device.

Various embodiments of the first aspect may comprise at least one feature from the following bulleted list:
- the apparatus is enabled to act as a client whose content is fully or at least partially controlled by the exercising device
- the apparatus is configured to store and process program code received from the exercising device
- the apparatus is capable of receiving parameters and/or logics from the exercising device
- the apparatus is capable of processing instructions received from the exercising device
- the apparatus is capable of starting calculations based on the received instructions
- the apparatus is capable of starting user interface methods based on the received instructions
- the apparatus is capable of receiving a recipe or instruction from the exercising device how to analyse movements of a user
- the recipe can be received from a server
- the apparatus is a first mobile device, a wrist-watch, a tablet (computer), a smartwatch, or a smartphone
- the apparatus is capable of controlling a music program or a music playlist stored in the memory of the exercising device or in the memory of a second mobile device such as a tablet or a smartphone
- the apparatus is configured to serve as a display of the exercising device
- the apparatus is configured to serve as an additional display of the exercising device
- the apparatus is configured to serve as a user interface of the exercising device
- the apparatus is configured to serve as an additional user interface of the exercising device
- the apparatus is configured to serve as a memory of the exercising device
- the apparatus is configured to serve as an additional memory of the exercising device
- the apparatus is configured to participate in the pairing process during a session with the exercising device the session is based on sensors of the apparatus and the exercising device the apparatus is configured to receive sensor data from the exercising device and to transmit in response input parameters to the exercising device the apparatus is capable of transmitting instructions to the exercising device, for example to change a speed of a part of the exercising device, to change a resistance of the exercising device, or to change a weight of the exercising device the apparatus is configured to receive the first signal and to transmit the second signal when a distance between the apparatus and the exercise device is in the range between 0 m-10 m, for example 5 m-10 m the apparatus is configured to transmit data to a server the apparatus is configured to receive data from a wearable sensor or any other external sensor the apparatus is configured to store at least a part of data received from a wearable sensor or any other external sensor time stamps associated with sensor data are contained in data received from a wearable sensor or any other external sensor the processing core of the apparatus is capable of arranging sensor data in an order depending on the time stamps associated with the sensor data the apparatus is configured to allow a user to remotely read-out at least a part of obtained sensor data the apparatus is configured to control parameters or functions of the exercising device the apparatus is capable of transmitting and receiving signals wirelessly the apparatus is configured to transmit and/or receive sensor data and associated time stamps to at least one of the server and the exercising device According to a second aspect of the present invention, there is provided an exercising device comprising at least one processing core, at least one memory including computer program code, the at least one memory and the computer program code being configured to, with the at least one processing core, cause the exercising device at least to transmit a first signal to an apparatus, receive a second signal from the apparatus, and participate in pairing with the exercise device.

Various embodiments of the second aspect may comprise at least one feature from the following bulleted list:

the exercising device is enabled to act as a server having control over the user interface of the apparatus the exercising device is configured to transmit program code to be stored and processed by the apparatus the exercising device is capable of transmitting parameters and/or logics to the apparatus the exercising device is capable of transmitting instructions to the apparatus the exercising device is capable of receiving data which has been input via a user interface of the apparatus the exercising device is capable of transmitting a recipe or an instruction to the apparatus how to analyse movements of a user recipe can be retrieved from a server by the exercising device the exercising device is an ergometer, a gym exercising device, a fitness device, a sports device, a weight lifting device, an exercise bike, a treadmill, a rowing machine, or a cross trainer the exercising device is configured to transmit data to the apparatus, which data is to be displayed on a display of the apparatus the exercising device is configured to participate in the pairing process during a session with the apparatus the session is based on sensors of the apparatus and the exercising device the exercising device is configured to transmit sensor data to the apparatus and to receive in response input parameters from the apparatus the exercising device is capable of receiving instructions from the apparatus the exercising device is configured to transmit the first signal and to receive the second signal when a distance between the apparatus and the exercise device is in the range between 0 m-10 m, for example 5 m-10 m the exercising device is configured to transmit data to a server the exercising device is configured to receive data from a wearable sensor or any other external sensor the exercising device is configured to store at least a part of data received from a wearable sensor or any other external sensor time stamps associated with sensor data are contained in data received from a wearable sensor or any other external sensor the processing core of the exercising device is capable of arranging sensor data in an order depending on the time stamps associated with the sensor data the exercising device is configured to allow a user to remotely read-out at least a part of obtained sensor data the exercising device is capable of transmitting and receiving signals wirelessly the exercising device is configured to transmit and/or receive sensor data and associated time stamps to at least one of a server and the apparatus Considerable advantages are obtained by means of certain embodiments of the present invention. An apparatus comprising at least one processing core and at least one memory including computer program code and an exercising device comprising at least one processing core and at least one memory including computer program code are provided. The apparatus and the exercising can form at least temporarily a unit in which the apparatus serves as a display, a user interface and/or a memory of the exercising device. According to certain embodiments of the present invention, the mobile device serves as a display of the exercising device. The mobile device may serve as the only display or as an additional display of the exercising device during the time period of a user session. According to certain other embodiments of the present invention, the mobile device serves as a user interface of the exercising device. The mobile device may serve as the only user interface or as an additional user interface of the exercising device during the time period of a user session.

A mobile device and the exercising device can temporarily form a unit during the time period of a user session, a training session or a sports session. According to an embodiment, an app which is related to a specific exercising device can be stored in the memory of the mobile device of a user. Settings of the app can be personalized. For example, when the user is bringing his/her mobile device to a gym, the user can start a user session using his/her own personalized settings. Personalized settings may include information about age, weight, height, gender, body mass index, maximum performance capacity, activity parameter, previous energy expenditure and maximum heart rate, for instance.

Also personalized exercise-guidance parameters such as an energy expenditure target, heart rate zones, activity zones, anaerobic threshold, fitness classification identifier and/or dehydration warning limits may be stored on the mobile device. Personalized data determined by sensors of the exercising device can further be stored in the memory of the mobile device and/or in the internet. Further, personalized data determined by sensors of the mobile device can be stored in the memory of the mobile device and/or in the internet. Determined data of the user, for example movement data or heart-beat rate data, can then be analysed at a later stage subsequent to the user session, training session or sports session. When another user is using the exercising device in the gym, his/her mobile device and the exercising device temporarily form a unit during the time period of another user session. Personalized settings can be used by this other user and personalized data can be stored in the memory of the respective mobile device and/or in the internet for further analysis. Consequently, it is not necessary to store any personalized data on the memory of the exercising device according to certain embodiments of the present invention.

According to another embodiment, no program code or a minimum amount thereof needs to be installed on the apparatus such as a wrist watch. The apparatus serves as a display and/or user interface for the exercising device. The procedure is controlled by the exercising device or the apparatus. Minimum system requirements are required for the apparatus. According to this embodiment, the input data is processed by the exercising device. The bidirectional communication link between the apparatus and the exercising device may be used to enable the exercising device to act as a server having control over the user interface and the apparatus to act as a client whose content is fully or at least partially controlled by the exercising device.

A comfortable user experience can be provided in accordance with at least some embodiments of the present invention. When the user changes the exercising device, for example in a gym, the displayed information on the display of the apparatus also automatically changes depending on the new exercising device. The exercising device can additionally receive further data from a server or via the internet. External sensor data can be analysed by the exercising device and content, for example information derived from the sensor data, can be automatically displayed on the apparatus.

According to certain embodiments, a temporarily combined unit can share a classification task. I.e. the exercising device has its own classification task to produce semantic events like 'lift', 'release', 'step' etc. Similarly, the apparatus has its own classification task to produce semantic events. The system creates a more comprehensive analysis of the user's actions to provide e.g. a deeper understanding of the user's biomechanical accuracy.

Certain embodiments of the present invention are applicable with regards to health care, in industry, in working environments, in sports, and the like.

EMBODIMENTS

Figure 1:
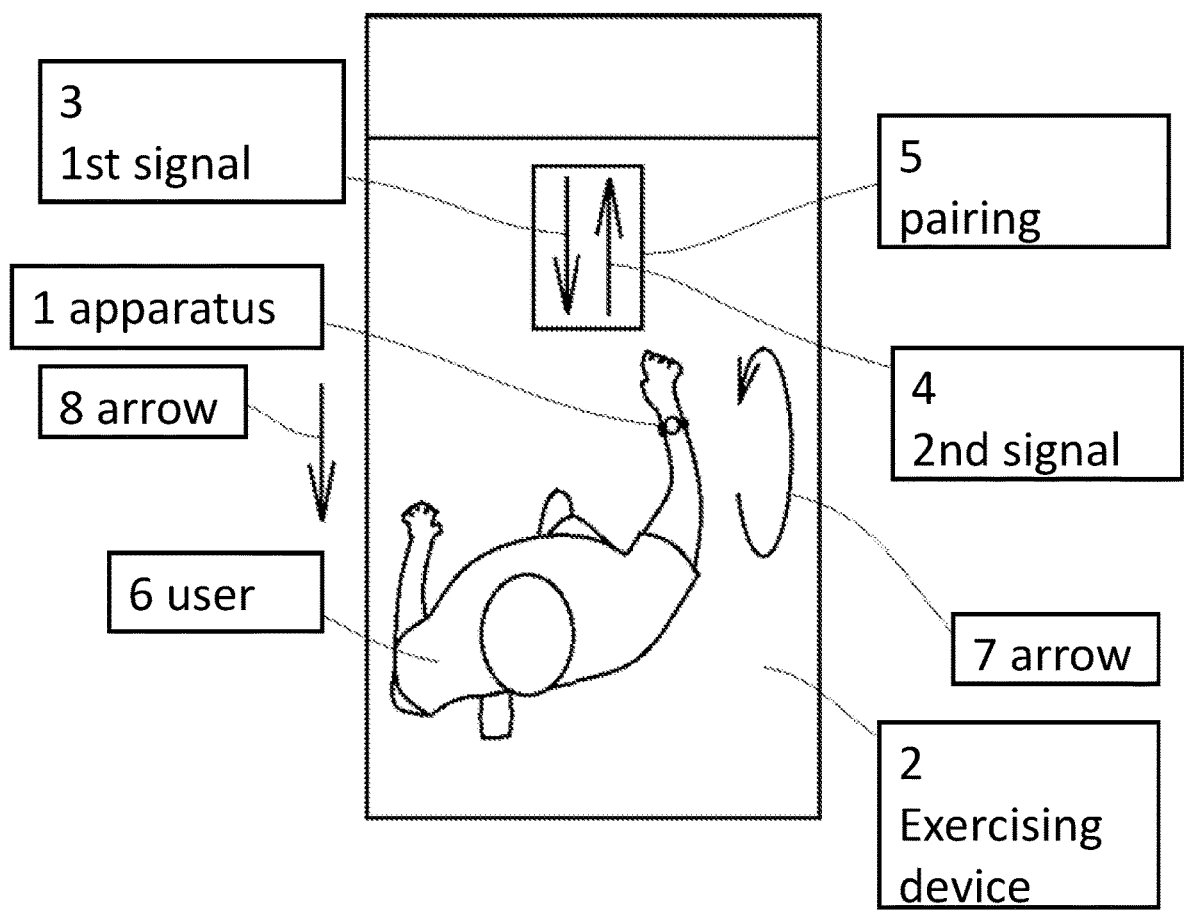
FIG. 1 illustrates a schematic top view of an apparatus in accordance with at least some embodiments of the present invention.

In FIG. 1 a schematic top view of an apparatus 1 in accordance with at least some embodiments of the present invention is illustrated. The shown apparatus 1 is a wrist-watch. The apparatus 1 comprises at least one processing core and at least one memory including computer program code. The at least one memory and the computer program code are configured to, with the at least one processing core, cause the apparatus 1 at least to receive a first signal 3 from an exercising device 2, process the received signal, respond to the received signal by transmitting a second signal 4 to the exercising device 2, and participate in a pairing process 5 with the exercise device 2.

In other words, when a user 6 wearing the wrist-watch 1 is located close to an exercising device 2 or starts to use the exercising device 2, the wrist-watch 1 and the exercising device start to communicate with each other. A first signal as indicated by arrow 3 from the exercising device 2 is transmitted to the wrist-watch 1. Then the received signal 3 is processed by the processing core of the wrist-watch 1. Subsequently, a second signal as indicated by arrow 4 is transmitted from the wrist-watch 1 to the exercising device 2. This process is called pairing 5. Data between the wrist-watch 1 and the exercising device 2 can now be transferred between the wrist-watch 1 and the exercising device 2. Data is typically transferred using low power wireless communication technology such as Bluetooth, Bluetooth Low Energy, or Wibree.

The exercising device 2 shown in FIG. 1 is a treadmill. The treadmill belt of the exercising device 2 may be moving with a specific speed as indicated by arrow 8 as a user 6 is running on the belt. At the same time, the arms of the runner 6 move cyclically as indicated by arrow 7. Data may be determined by the sensors of the wrist-watch 1. Examples of such determined data are a heart-beat rate, number of steps during a certain period of time, or acceleration data. Data may also be determined by sensors of the exercising device 2 and transmitted to the apparatus 1. An example of such data is the speed of the moving treadmill belt of the exercising device 2. The information about the speed of the treadmill belt may be transmitted from the exercising device 1 to the wrist-watch 1. The information about the speed of the treadmill belt may then be displayed on the wrist-watch. In other words, the wrist-watch 1 is configured to serve as a display of the exercising device 2. Of course, also data determined by at least one sensor of the wrist-watch 1 may be displayed on the display of the wrist-watch. The user 6 may further choose which data is displayed.

According to certain embodiments, the exercising device 2 may also comprise an additional display and data may be transmitted from the wrist-watch 1 to the exercising device 2. A user 6 may choose which information is shown on the display of the exercising device 2 and which information is at the same time displayed on the display of the wrist-watch 1. In other words, the user 6 may choose which sensor data is displayed on the display of the wrist-watch 1 and which sensor data is displayed on the display of the exercising device 2.

According to certain other embodiments, the apparatus 1 is configured to control parameters or functions of the exercising device 2 after the pairing process 5. In the shown example, a user 6 may control the speed of the treadmill belt of the exercising device 2 as indicated by arrow 8 via a user interface of the wrist-watch 1. A user interface of the wrist watch 1 may be a touchscreen or at least one button, for instance. User instructions to change the speed of the treadmill belt may be transmitted from the wrist-watch 1 to the exercising device 2 and processed by the exercising device 2, thus causing the exercising device 2 to change the speed of the treadmill belt. According to this embodiment, the procedure is typically fully or at least partially controlled by the exercising device 2 such that no program code or a minimum amount thereof needs to be installed on the mobile device 1. The mobile device 1 serves as a user interface for the exercising device 2. In other words, a computer program comprising program instructions which, when loaded into the exercising device 2, cause e.g. graphical user interface data to be determined for the mobile device 1 is provided. The graphical user interface data is wirelessly transmitted to the mobile device 1 from the exercising device 2 to provide at least one user interface functionality on the mobile device 1. Then data corresponding to user input is received and wirelessly transmitted to the exercising device 2. Minimum system requirements such as processing capacity and memory capacity are required for the mobile device 1. According to this embodiment, the input data is completely or at least partially processed by the exercising device 2. The bidirectional communication link between the mobile device 1 and the exercising device 2 may be used to enable the exercising device 2 to act as a server having control over the user interface and the mobile device 1 to act as a client whose content is fully or at least partially controlled by the exercising device 2.

Of course, the apparatus 1 and/or exercising device 2 may be also configured to store and process sensor data received from a wearable sensor or any other external sensor, for example a MOVESENSE sensor. Such sensor data may be wirelessly transferred to the apparatus 1 or the exercising device 2 directly or to the apparatus 1 first and then to the exercising device 2.

According to a certain embodiment, an external sensor (not shown), for example a MOVESENSE sensor, is attached to a user and connected to the apparatus 1, for example a wrist watch 1. When the user comes to an exercising device 2, the apparatus 1 automatically displays information. Simultaneously, the apparatus 1 receives instructions from the exercising device 2. However, also the exercising device 2 may receive data from the apparatus 1 and/or the external sensor. The data may, for example, include personal data, sensor data and/or external sensor data. The data is typically processed by the exercising device 2. This kind of user experience is automatically created. When the user changes the exercising device 2, for example in a gym, the displayed information on the display of the apparatus 1 also automatically changes. The exercising device 2 can additionally receive further data from a server or via the internet. External sensor data can be analysed by the exercising device and content, for example information derived from the sensor data, can be automatically displayed on the apparatus 1. In such a situation, the exercising device 2 may be used to enable the exercising device 2 to act as a server having control over the user interface and the mobile device 1 to act as a client whose content is fully or at least partially controlled by the exercising device 2.

Figure 2:
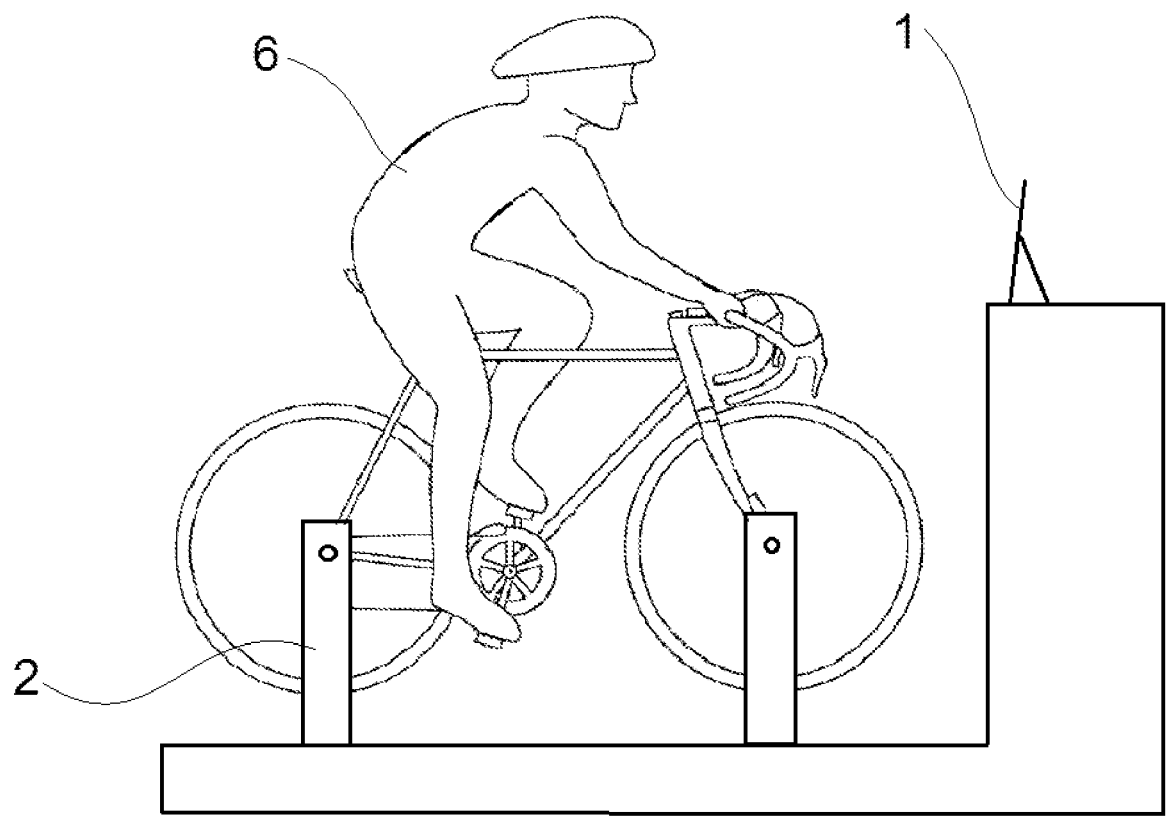
FIG. 2 illustrates a schematic side view of another apparatus in accordance with at least some embodiments of the present invention.

In FIG. 2 a schematic side view of another apparatus 1 in accordance with at least some embodiments of the present invention is illustrated. The shown apparatus 1 is a mobile device such as a tablet or other mobile device. The shown exercising device 2 is an ergometer or indoor exercise bike. After the pairing process as described above in connection with FIG. 1, parameters and/or logics such as an app are transmitted from the exercising device 2 to the apparatus 1. The apparatus 1 is configured to store and process program code received from the exercising device 2. The apparatus 1 is configured to serve as a display of the exercising device 2.

For example, a video simulation of a cycling track may be displayed on the display of the apparatus 1. Thus, the user 6 can cycle along the simulated track. Sensors of the exercising device 2 may determine the cycling speed of the user 6, for example. The sensor data of the exercising device 2 is then transmitted to the apparatus 1. The sensor data can be used as input data for the video simulation displayed on the apparatus 1. In other words, the user 6 can cycle along the virtual track with varying speeds. The visualization of the virtual cycling simulation is calculated based on the speed data obtained from the sensor data of the exercising device 2. On the other side, data may be transmitted from the apparatus 1 to the exercising device 2, thus causing the exercising device to change a parameter. Altitude data along the virtual track stored in the app may be provided, for instance. The altitude data can be used as input data for the parameters of the exercising device 2 as a function of time. When the data is received by the exercising device 2, it causes the exercising device 2 to change the resistance of the exercise bike during cycling along the virtual track. In other words, cycling upwards or downwards along the virtual track can be simulated. The exercising device 2 is configured to transmit sensor data to the apparatus 1 and to receive in response input parameters from the apparatus 1. Consequently, cycling along a virtual track, for example a passage of the Tour de France, can be simulated.

The exercising device 2 may be, for example, located in a gym and different users may subsequently cycle along the virtual track. When each user bring his/her own apparatus 1 to the gym, for each user a period of time may be determined by the app for cycling from the beginning of the virtual track to the end of the virtual track. The period of time for each user may then be transmitted from the respective apparatus 1 to the exercising device 2 and stored in a memory of the exercising device 2. The different periods of time may be ranked and listed so that a user can see his/her results in comparison to the results of other users. Thus, it is possible to simulate a cycling competition, for instance.

Of course, the apparatus 1 may also be used for displaying only information such as cycling speed, length of cycling session period or for selecting a cycling resistance of the exercising device 2.

Data determined by sensors of the exercising device 2 may be received by and stored in the apparatus 1. Alternatively, data determined by sensors of the exercising device 2 may be received by the apparatus and stored in the cloud. Thus, the user 6 can analyse the stored data at a later stage by reading out the memory of the apparatus 1 or viewing a webpage in the internet.

Figure 3:
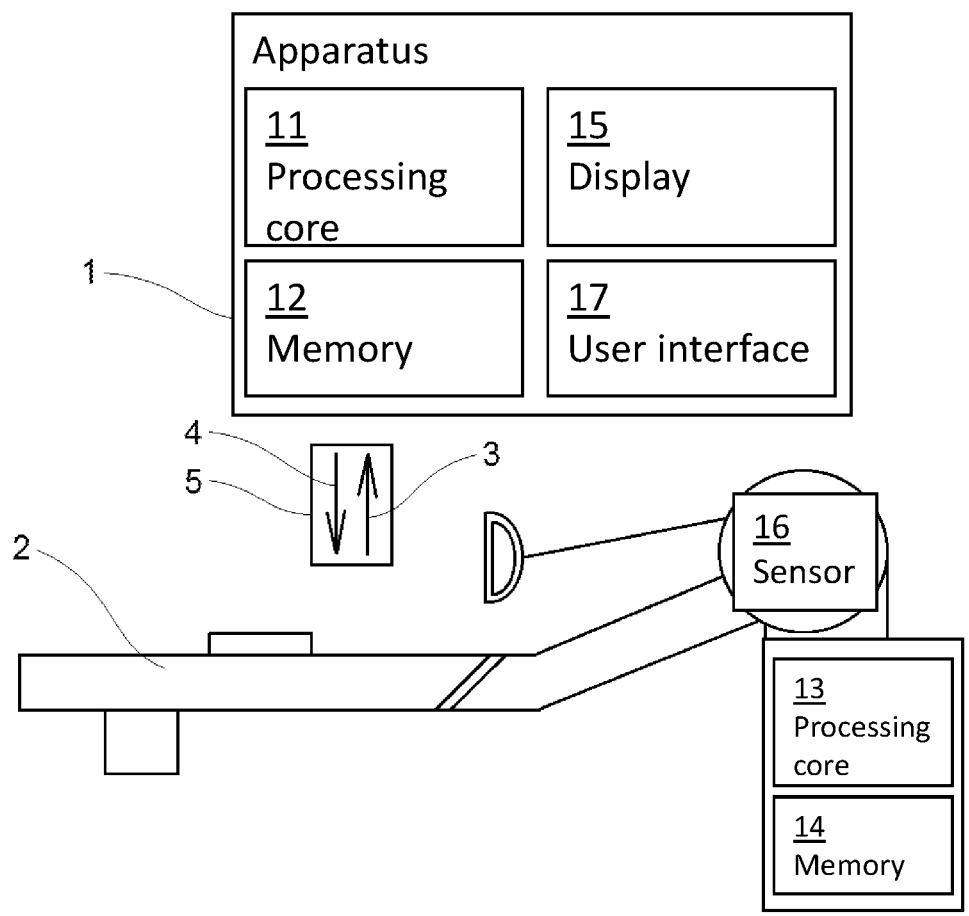
FIG. 3 illustrates a schematic side view of an exercising device in accordance with at least some embodiments of the present invention.

In FIG. 3 a schematic side view of an exercising device 2 in accordance with at least some embodiments of the present invention is illustrated. In the shown embodiment, the exercising device 2 is a rowing machine. The apparatus 1 may be a tablet computer, for instance. The exercising device 2 comprises at least one processing core 13 and at least one memory 14 including computer program code. The at least one memory 14 and the computer program code are configured to, with the at least one processing core 13, cause the exercising device 2 at least to transmit a first signal 3 to an apparatus 1, receive a second signal 4 from the apparatus 1, and participate in pairing 5 with the apparatus 1.

Subsequent to the pairing process 5, program code to be stored and processed by the apparatus 1 can be transmitted from the exercising device 2. Parameters and/or logics such as a rule engine, an app, a classification recipe or a html web page can be transmitted to the apparatus, for instance.

For example, an app may be transmitted to the apparatus 1. A user can select a training program with the help of the app. During the training session, the exercising device 2 may, for example, transmit a recipe or an instruction to the apparatus 1 how to analyse movements of a user 6. The movements of the user may be determined or recorded using sensors of the exercising device 2. Examples of such sensors of the exercising device are force sensors and acceleration sensors. Data determined by the sensors of the exercising device 2 may be shown on a display 15 of the apparatus 1.

A user can further input data using a user interface 17 of the apparatus 1. A user interface 17 may be, for example, a touchscreen, a button, a keyboard or an optical system analysing gestures of the user. The exercising device 2 is capable of receiving the data which has been input via the user interface 17 of the apparatus 1. The exercising device 2 is capable of receiving instructions from the apparatus 1. For example, another training program may be selected.

According to certain embodiments, a first exercising device 2 and a first apparatus 1 in accordance with at least some embodiments form a first unit and a second exercising device 2 and a second apparatus 1 in accordance with at least some embodiments form a second unit. The first unit and the second unit are capable of communicating with each other. For example, rowing of a rowing boat having two seats can be simulated. Subsequent to starting of a specific training program, two users simultaneously using respective exercising devices have to synchronize their movements in order to row a virtual rowing boat. A first user is then virtually in the position of the person sitting in front of the other person. Thus, a sports team can train rowing of a rowing boat, for example in winter time when training with a real rowing boat is not possible due to weather conditions.

Figure 4:
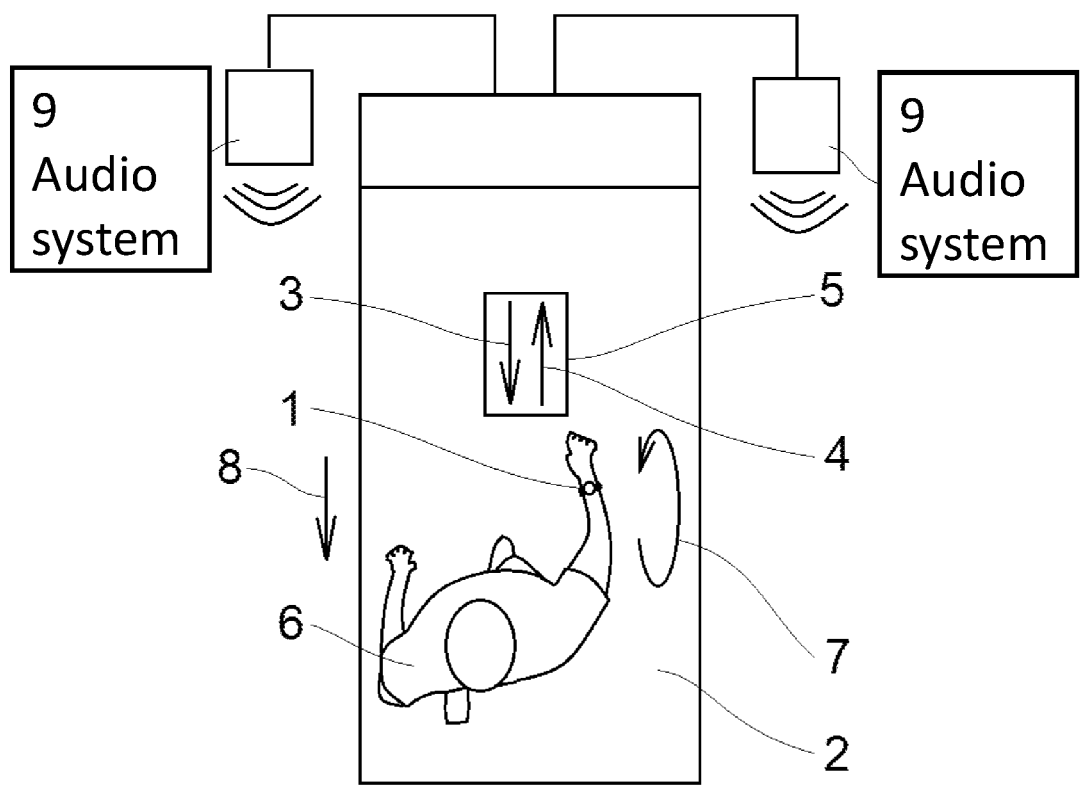
FIG. 4 illustrates a schematic top view of a further apparatus in accordance with at least some embodiments of the present invention.

In FIG. 4 a schematic top view of a further apparatus 1 in accordance with at least some embodiments of the present invention is illustrated. The exercising device 2 includes an audio system 9. After the pairing process 5 as described above in connection with FIG. 1, a music program can be started or stopped, a volume of music can be controlled and/or a title can be selected using the mobile device 1 in the form of a wrist-watch 1. According to this embodiment, the procedure is typically fully or at least partially controlled by the exercising device 2 such that no program code or a minimum amount thereof needs to be installed on the mobile device 1. The mobile device 1 serves as a user interface for the exercising device 2. In other words, a computer program comprising program instructions which, when loaded into the exercising device 2, cause e.g. graphical user interface data to be determined for the mobile device 1 is provided. The graphical user interface data is wirelessly transmitted to the mobile device 1 from the exercising device 2 to provide at least one user interface functionality on the mobile device 1. Then data corresponding to user input is received and wirelessly transmitted to the exercising device 2. Minimum system requirements such as processing capacity and memory capacity are required for the mobile device 1. According to this embodiment, the input data is completely or at least partially processed by the exercising device 2. The bidirectional communication link between the mobile device 1 and the exercising device 2 may be used to enable the exercising device 2 to act as a server having control over the user interface and the mobile device 1 to act as a client whose content is fully or at least partially controlled by the exercising device 2.

Alternatively, a provided further, second mobile device (not shown), for example a smartphone, may include an audio system. In such a case, a music program can be started or stopped, a volume of music can be controlled and/or a title can be selected using the wrist-watch 1 after the pairing process 5 between the apparatus 1 and the exercising device 2. In other words, the apparatus 1 may be used to additionally control functions of a further second mobile device. According to this embodiment, the procedure is typically fully or at least partially controlled by the second mobile device such that no program code or a minimum amount thereof needs to be installed on the mobile device 1 such as a wrist-watch. The mobile device 1 serves as a user interface for the second mobile device. In other words, a computer program comprising program instructions which, when loaded into the second mobile device, cause e.g. graphical user interface data to be determined for the mobile device 1 is provided. The graphical user interface data is wirelessly transmitted to the mobile device 1 from the second mobile device to provide at least one user interface functionality on the mobile device 1. Then data corresponding to user input is received and wirelessly transmitted to the second mobile device. Minimum system requirements such as processing capacity and memory capacity are required for the mobile device 1. According to this embodiment, the input data is completely or at least partially processed by the second mobile device. The bidirectional communication link between the mobile device 1 and the second mobile device may be used to enable the second mobile device to act as a server having control over the user interface and the mobile device 1 to act as a client whose content is fully or at least partially controlled by the second mobile device.

Figure 5:
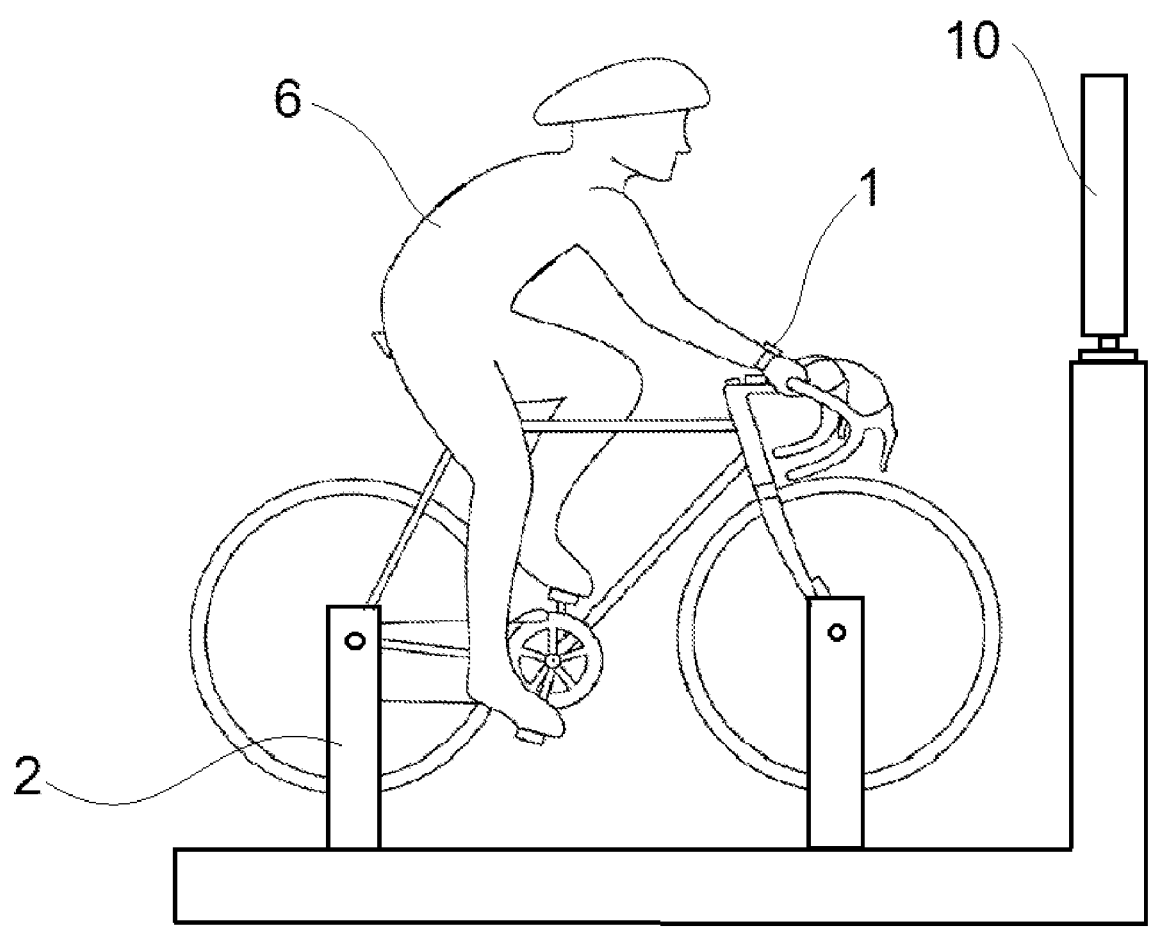
FIG. 5 illustrates a schematic side view of another exercising device in accordance with at least some embodiments of the present invention.

In FIG. 5 a schematic side view of another exercising device 2 in accordance with at least some embodiments of the present invention is illustrated. The shown exercising device 2 is an ergometer in the form of an indoor exercise bike. The exercising device 2 comprises at least one processing core and at least one memory including computer program code. The at least one memory and the computer program code are configured to, with the at least one processing core, cause the exercising device at least to transmit a first signal to an apparatus 1, receive a second signal from the apparatus 1, and participate in pairing with the apparatus 1. The exercising device 2 further comprises a video system 10. The video system 10 may be, for example, a TV, a tablet, or a PC. The mobile device 1 may be used as a remote control of the video system 10.

A wrist-watch is shown as the apparatus 1. Typically, the exercising device 2 is configured to transmit the first signal and to receive the second signal when a distance between the apparatus 1 and the exercise device 2 is about 0 m-10 m. In other words, the pairing process is activated when a user 6 with the wrist-watch 1 is moving closer to the exercising device 2. After the pairing process between the apparatus 1 and the exercising device 2, data can be transmitted between the apparatus 1 and the exercising device 2. For example, the user 6 may select a TV channel to be shown on the video system 10 by the wrist-watch 1. The wrist-watch 1 can therefore serve as a remote control when cycling. Alternatively, data obtained by sensors of the apparatus 1, for example heart beat data, and data obtained by sensors of the exercising device 2, for example speed data, may be displayed on the video system 10. The exercising device 2 is configured to participate in the pairing process during a session with the apparatus 1. The session is based on sensors of the apparatus 1 and the exercising device 2.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in displaying of sensor data determined by at least one sensor of an exercising device and at least one sensor of a mobile device. Certain embodiments of the present invention are applicable in health care, in industry, in working environments, sports, etc.

REFERENCE SIGNS LIST 1 apparatus
2 exercising device
3 first signal
4 second signal
5 pairing
6 user
7 arrow
8 arrow
9 audio system
10 video system
11 processing core of apparatus
12 memory of apparatus
13 processing core of exercising device
14 memory of exercising device
15 display
16 sensor
17 user interface
18 server

The invention claimed is:

1. A wrist watch comprising at least one processing core, at least one memory including computer program code, the at least one memory and the computer program code being configured to, with the at least one processing core, cause the wrist watch at least to:
   receive a first signal from a stationary exercising device,
   process the received signal,
   respond to the received signal by transmitting a second signal to the stationary exercising device, and
   participate in a pairing process with the stationary exercising device, wherein the wrist watch is configured to participate in the pairing process during a user session with the stationary exercising device based on sensor data of the wrist watch and the stationary exercising device,
wherein the wrist watch is enabled to act as a client whose content is fully or at least partially controlled by the stationary exercising device, and
wherein the wrist watch is capable of processing instructions received from the stationary exercising device after the pairing process,
wherein the pairing process takes place automatically when the user starts using the stationary exercising device, and
wherein the sensor data of a different exercise device is used in the pairing process when the user changes exercising devices.

2. The wrist watch according to claim 1, wherein the wrist watch is enabled to act as a client whose content is fully or at least partially controlled by the stationary exercising device which acts as a server having control of a user interface of the wrist watch.

3. The wrist watch according to claim 1, wherein the wrist watch is configured to store and process program code received from the stationary exercising device.

4. The wrist watch according to claim 1, wherein the wrist watch is capable of receiving parameters and/or logics from the stationary exercising device.

5. The wrist watch according to claim 1, wherein the wrist watch is capable of starting calculations based on the received instructions.

6. The wrist watch according to claim 1, wherein the wrist watch is capable of starting user interface methods based on the received instructions.

7. The wrist watch according to claim 1, wherein the wrist watch is capable of receiving instructions from the stationary exercising device how to analyze movements of a user.

8. The wrist watch according to claim 1, wherein the wrist watch is capable of controlling a music program or a music playlist stored in the memory of the exercising device or in the memory of a second mobile device.

9. The wrist watch according to claim 1, wherein the wrist watch is configured to serve as a display, a user interface and/or a memory of the stationary exercising device.

10. The wrist watch according to claim 1, wherein the wrist watch is configured to receive sensor data from the stationary exercising device and to transmit in response input parameters to the stationary exercising device.

11. A stationary exercising device comprising at least one processing core, at least one memory including computer program code, the at least one memory and the computer program code being configured to, with the at least one processing core, cause the stationary exercising device at least to:
transmit a first signal to a wrist watch,
receive a second signal from the wrist watch, and
participate in pairing with the wrist watch, wherein the stationary exercising device is configured to participate in the pairing process during a user session with the wrist watch based on sensor data of the wrist watch and the stationary exercising device,
wherein the stationary exercising device is enabled to act as a server which fully or at least partially controls content of the wrist watch, and
wherein the stationary exercising device is capable of transmitting instructions to the wrist watch after the pairing process,
wherein the pairing process takes place automatically when the user starts using the stationary exercising device, and wherein the sensor data of a different exercise device is used in the pairing process when the user changes exercising devices.

12. The stationary exercising device according to claim 11, wherein the stationary exercising device is enabled to act as a server having control over the user interface of the wrist watch.

13. The exercising device according to claim 11, wherein the stationary exercising device is configured to transmit program code to be stored and processed by the wrist watch.

14. The stationary exercising device according to claim 11, wherein the stationary exercising device is capable of transmitting parameters and/or logics to the wrist watch.

15. The stationary exercising device according to claim 11, wherein the stationary exercising device is capable of receiving data which has been input via a user interface of the wrist watch.

16. The stationary exercising device according to claim 11, wherein the stationary exercising device is capable of transmitting a recipe or an instruction to the wrist watch how to analyze movements of a user.

17. The stationary exercising device according to claim 11, wherein the stationary exercising device is an ergometer, a weight lifting device, an exercise bike, a treadmill, a rowing machine, or a cross trainer.

18. The stationary exercising device according to claims 11, wherein the stationary exercising device is configured to transmit data to the wrist watch, which data is to be displayed on a display of the wrist watch.

19. The stationary exercising device according to claims 11, wherein the stationary exercising device is configured to transmit sensor data to the wrist watch and to receive in response input parameters from the wrist watch.

20. The stationary exercising device according to claim 11, wherein the stationary exercising device is capable of receiving instructions from the wrist watch.

* * * * *